(12) United States Patent  (10) Patent No.: US 8,676,537 B2
Liu et al.  (45) Date of Patent: Mar. 18, 2014

(54) PORTABLE WIRELESS SENSOR (75) Inventors: Hsu-Shui Liu, Pingtung (TW);
Yeh-Chieh Wang, Hsinchu (TW);
Jiun-Rong Pai, Jhubei (TW)

(73) Assignee: Taiwan Semiconductor Manufacturing Company, Ltd., Hsin-Chu (TW)

( * ) Notice: Subject to any disclaimer, the term of this patent is extended or adjusted under 35 U.S.C. 154(b) by 461 days.

(21) Appl. No.: 12/610,280

(22) Filed: Oct. 31, 2009

(65) Prior Publication Data

US 2011/0035186 A1  Feb. 10, 2011

Related U.S. Application Data (60) Provisional application No. 61/232,225, filed on Aug. 7, 2009.

(51) Int. Cl.
*G06F 15/00* (2006.01)
*G06F 19/00* (2011.01)

(52) U.S. Cl.
USPC .......................................... 702/182; 700/121

(58) Field of Classification Search
USPC ....................................................... 702/182
See application file for complete search history.

(56) References Cited

U.S. PATENT DOCUMENTS

| 6,642,853 | B2 | 11/2003 | Hunter |
| 7,360,463 | B2 * | 4/2008 | Renken ........................ 73/866.1 |
| 7,840,305 | B2 | 11/2010 | Behr et al. |
| 2005/0011611 | A1 * | 1/2005 | Mahoney et al. ........ 156/345.24 |
| 2005/0039852 | A1 * | 2/2005 | Roche et al. ............. 156/345.24 |
| 2006/0171561 | A1 * | 8/2006 | Ramsey et al. ............... 382/103 |
| 2006/0174720 | A1 * | 8/2006 | Renken et al. ............... 73/866.1 |
| 2007/0000310 | A1 * | 1/2007 | Yamartino et al. ............. 73/40.7 |
| 2007/0224712 | A1 | 9/2007 | Kaushal et al. |
| 2008/0004723 | A1 | 1/2008 | Fax et al. |
| 2008/0097646 | A1 | 4/2008 | Ramsey et al. |

OTHER PUBLICATIONS

SIPO Office Action of Feb. 29, 2012, Appl. No. 201010170245.0.

* cited by examiner

*Primary Examiner* — Bryan Bui
(74) *Attorney, Agent, or Firm* — Haynes and Boone, LLP (57) ABSTRACT The present disclosure provides an apparatus for fabricating a semiconductor device. The apparatus includes a portable device. The portable device includes first and second sensors that respectively measure first and second fabrication process parameters. The first fabrication process parameter is different from the second fabrication process parameter. The portable device also includes a wireless transceiver that is coupled to the first and second sensors. The wireless transceiver receives the first and second fabrication process parameters and transmits wireless signals containing the first and second fabrication process parameters.

20 Claims, 6 Drawing Sheets

PORTABLE WIRELESS SENSOR

PRIORITY DATA

This application claims priority to Provision Application Ser. No. 61/232,225, filed on Aug. 7, 2009, entitled "PORTABLE WIRELESS SENSOR," the entire disclosure of which is incorporated herein by reference.

TECHNICAL FIELD

The present disclosure relates generally to a sensor, and more particularly, to a portable wireless sensor used in semiconductor fabrication.

BACKGROUND

Semiconductor fabrication requires a plurality of fabrication tools. These fabrication tools use internal or external sensors that measure fabrication process parameters such as temperature, current, voltage, or pressure. However, the parameters that the fabrication tools are capable of measuring are limited by vendor designs, which often do not provide the capability to measure some of the desired key process parameters. In addition, the sensors usually are wired and are difficult to disassemble. Furthermore, the sensors are usually designed to sense only a single parameter, and it is difficult to integrate additional functionalities into the sensors.

Therefore, while existing semiconductor fabrication sensors have been generally adequate for their intended purposes, they have not been entirely satisfactory in every aspect.

SUMMARY

One of the broader forms of the present disclosure involves an apparatus for fabricating a semiconductor device. The apparatus includes a portable device that includes, first and second sensors that measure first and second fabrication process parameters, the first fabrication process parameter being different from the second fabrication process parameter; and a wireless transceiver that is coupled to the first and second sensors, the wireless transceiver receiving the first and second fabrication process parameters and transmitting wireless signals containing the first and second fabrication process parameters.

Another of the broader forms of the present disclosure involves an apparatus for fabricating a semiconductor device. The apparatus includes a portable device that includes, first and second sensors that measure first and second processing data in an analog form; a signal converter that converts the first and second processing data from the analog form into a digital form; a micro-controller that modulates the measured first and second processing data using a predetermined modulation scheme; and a wireless transceiver that transmits wireless signals containing the modulated first and second processing data.

Still another of the broader forms of the present disclosure involves a method of fabricating a semiconductor device. The method includes measuring a first fabrication process parameter using a first sensor; measuring a second fabrication process parameter using a second sensor, the second fabrication process parameter being different from the first fabrication process parameter; and transmitting wireless signals containing the measured first and second fabrication process parameters using a wireless transceiver; and configuring the wireless transceiver and the first and second sensors so that the wireless transceiver and the first and second sensors are integrated into a single portable device.

BRIEF DESCRIPTION OF THE DRAWINGS

Aspects of the present disclosure are best understood from the following detailed description when read with the accompanying figures. It is emphasized that, in accordance with the standard practice in the industry, various features are not drawn to scale. In fact, the dimensions of the various features may be arbitrarily increased or reduced for clarity of discussion.

DETAILED DESCRIPTION

It is understood that the following disclosure provides many different embodiments, or examples, for implementing different features of various embodiments. Specific examples of components and arrangements are described below to simplify the present disclosure. These are, of course, merely examples and are not intended to be limiting. For example, the formation of a first feature over or on a second feature in the description that follows may include embodiments in which the first and second features are formed in direct contact, and may also include embodiments in which additional features may be formed between the first and second features, such that the first and second features may not be in direct contact. In addition, the present disclosure may repeat reference numerals and/or letters in the various examples. This repetition is for the purpose of simplicity and clarity and does not in itself dictate a relationship between the various embodiments and/or configurations discussed.

Figure 1:
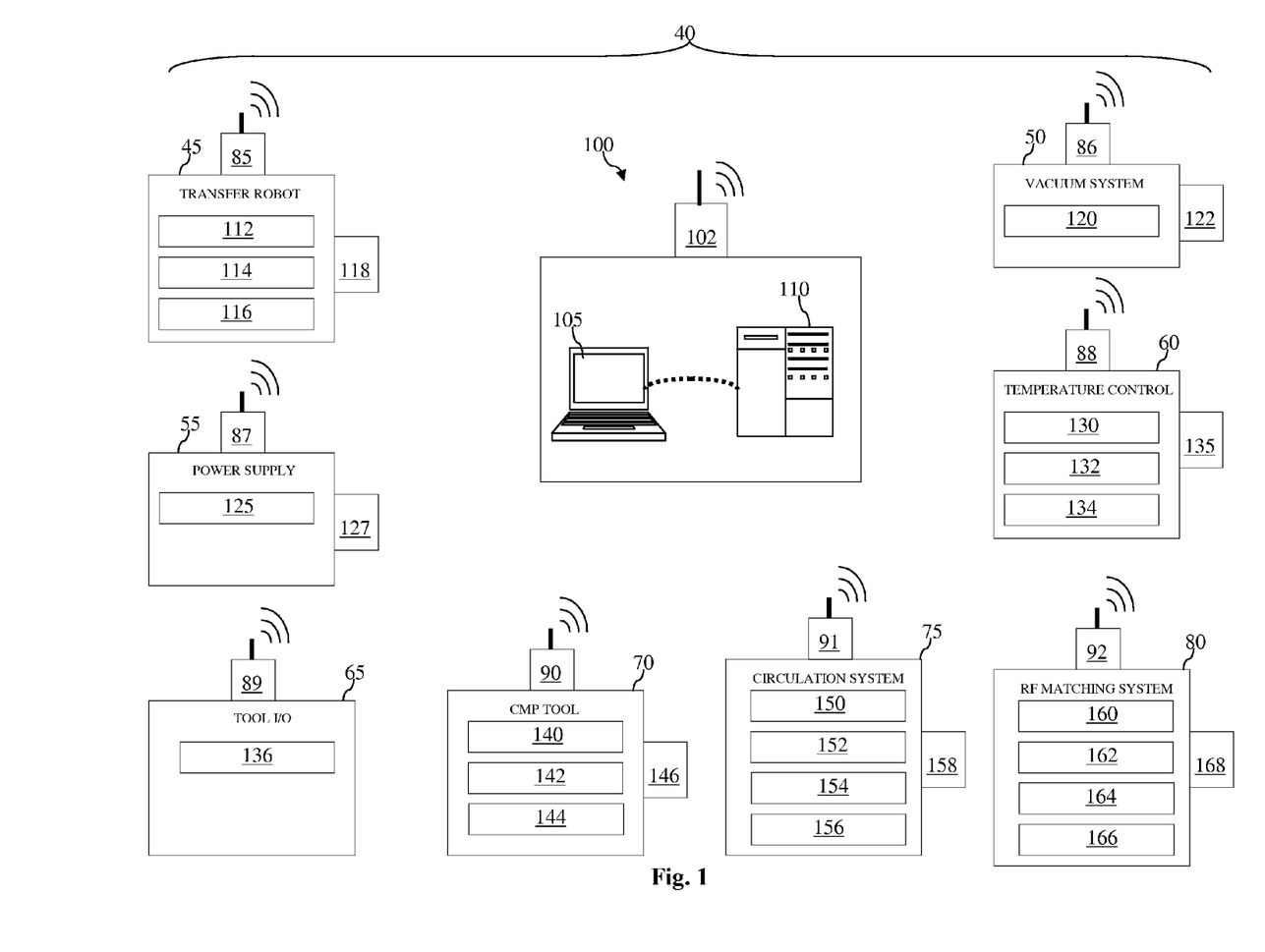
FIG. 1 is a diagrammatic view of a semiconductor fabrication system.

Illustrated in FIG. 1 is a diagrammatic view of a semiconductor fabrication system 40. The semiconductor fabrication system 40 includes a plurality of semiconductor fabrication tools. In an embodiment, the semiconductor fabrication system 40 includes a transfer robot 45, a vacuum system 50, a power supply 55, a temperature control 60, an input/output (I/O) tool 65, a chemical-mechanical polishing (CMP) tool 70, a circulation system 75, and a radio frequency (RF) matching system 80. One or more sensors are detachably coupled to each of the fabrication tools 45-80. These sensors are used to collect fabrication data (also known as fabrication process parameters), the details of which will be discussed below. The fabrication tools 45-80 also include wireless transceivers 85, 86, 87, 88, 89, 90, 91, and 92, respectively. The wireless transceivers 85-92 each are a blue-tooth transceiver in the embodiment shown in FIG. 1, but may be transceivers of different technologies in alternative embodiments, such as Wi-Fi or USB. The wireless transceivers 85-92 are each electrically coupled to the respective sensors 112-166 in the respective fabrication tools 45-80, so that the transceivers receive fabrication data collected by the sensors. In an embodiment, the wireless transceivers 85-92 are integrated into the sensors on the respective fabrication tools 45-80.

The semiconductor fabrication system 40 further includes a diagnostic tool 100. The diagnostic tool 100 includes a wireless transceiver 102, a data miner 105, and a centralized server 110. The wireless transceiver 102 is similar to the transceivers 85-92 and is electrically coupled to the data miner 105. The data miner 105 in the present embodiment is a portable computing device, for example a laptop. The data miner 105 is electrically coupled to the centralized server 110, which in the present embodiment is a Computer Integration Manufacturing (CIM) system used for monitoring and controlling semiconductor fabrication processes. In alternative embodiments, the data miner 105 and the centralized server 110 may be implemented as other suitable processing and computing devices and may be integrated as a single unit.

The sensors in each of the fabrication tools 45-80 will now be described in more detail. The transfer robot 45 includes a current sensor 112, a pressure sensor 114, a vibration sensor (also referred to as a motion sensor) 116, and an I/O interface 118. To move objects such as wafers during a fabrication process, the transfer robot 45 uses a motor (not illustrated) that runs on electricity. The current sensor 112 is used to sense the amount of current in the motor. If the sensed current is outside of a predetermined normal range, it indicates a problem with the operation of the motor. For example, if the sensed current is too high, the motor may be overloaded and may be in danger of failing. The transfer robot 45 may also have mechanical "arms" that use a vacuum pipe (not illustrated). The amount of pressure inside the vacuum pipe is monitored by the pressure sensor 114, so that problems with the vacuum pipe such as jams, snaps, or leaks will be detected. The vibration sensor 116 helps gauge the performances and conditions of various components of the transfer robot 45 by sensing the vibration of these components.

The vacuum system 50 controls internal pressures of various types of equipment of a semiconductor fabrication system, such as the fabrication tools of the fabrication system 40. The vacuum system 50 includes pressure sensors 120 (for production chamber and pumping line) and an I/O interface 122. The pressure sensors 120 are used to monitor pumping speed, gas partial pressure, and chamber pressure (if a vacuum chamber is used for the vacuum system 50) of the vacuum system 50. The chamber pressure is correlated to an angle of the valve used to adjust the pressure of the chamber. Thus, tuning the valve angle in turn regulates the pressures of the vacuum system 50. The reading from the pressure sensors 120 allows precise turning of the valve angles. Further, valve angles for multiple chambers can be matched so that the pressures inside these chambers are the same.

The power supply 55 provides electrical power to various types of equipment of a semiconductor fabrication system, such as the fabrication tools of the fabrication system 40. The power supply 55 includes a power sensor 125 and an I/O interface 127. The power sensor 125 monitors and compares the amount of input power ("line-in" power) and amount of output power of the power supply 55. The reduction of power between the input power and the output power is the power loss. If the power loss becomes excessively high, it means some components of the fabrication tool are close to failure.

The temperature control 60 regulates the temperatures of various types of equipment of a semiconductor fabrication system, such as the fabrication tools of the fabrication system 40. The temperature control 60 includes current sensors 130, a resistance sensor 132, temperature sensors 134, and an I/O interface 135. The temperature control 60 uses a heating device (such as a resistance heater, not illustrated) to generate heat and a cooling device (such as a refrigeration compressor, not illustrated) to generate a cooling flow (coolant or de-ionized water). The heating and cooling devices both run on electrical current, and the amount of current in these devices is monitored by the current sensors 130. As discussed above with reference to the other current sensors, the current sensors 130 will detect a problem in the heating and cooling devices based on the amount of current measured. Further, the resistance of the heating device is measured by the resistance sensor 132, which will also help indicate whether a problem exists in the heating device. The temperature sensors 134 include thermocouples that are coupled to the fabrication tool in different internal and external locations. Thus, the temperatures throughout the fabrication tool are obtained. If the measured temperature at a specific location is too high or too low, the temperature setting is adjusted to address this condition.

The I/O tool 65 includes external sensors 136 that are installed on fabrication tools. The external sensors 136 are used to measure desired data (fabrication process parameters) that a given fabrication tool either does not have the capability to measure or lacks a sufficient number of I/O ports for routing. Thus, the external sensors measure these parameters and provide a simulated I/O port to a user. The I/O tool 65 assigns a system variable identification (SVID) to the measured parameters, so that these parameters will be recognized by the fabrication system 40 during later processing. As examples, the external sensors 136 may be flow meters installed on a circulation loop to ensure steady process conditions, or differential pressure manometers installed on exhaust pipes to guarantee appropriate heat loss and flow pattern, or thermocouples installed on a chamber housing/lid/chuck to compare thermo uniformity. In an embodiment, these external sensors 136 may include the sensors 112-134 discussed above as well as the sensors that will be discussed below shortly.

The CMP tool 70 is used to polish and remove surface layer of a wafer. The CMP tool 70 includes vibration sensors 140, a temperature sensor 142, a resistance sensor 144, and an I/O interface 146. The vibration sensors 40 are used to monitor vibrations of various components of the CMP tool 70, the temperature sensor 142 is used to monitor the temperature of a pad surface (used to polish the wafer, not illustrated), and the resistance sensor 144 is used to monitor the resistance of a de-ionized water rinse, so that the CMP process is ensured to progress smoothly. The CMP tool 70 will be discussed in more detail later as an example of the fabrication tools.

The circulation system 75 is used to perform various chemical processes in semiconductor fabrication, such as etching that is carried out in an etching tank (not illustrated) having an etching solution. The circulation system 75 includes a flow rate sensor 150, a temperature sensor 152, a radiation sensor 154, a level sensor 156, and an I/O interface 158. The flow rate sensor 150 and the temperature sensor 152 are used to monitor the flow rate and the temperature of the etching solution, respectively. The concentration (also referred to as consistency) of the etching solution is correlated to a spectrum of radiation (such as light) that is associated with the etching solution. The spectrum of radiation can be detected by the radiation sensor 154, which may be implemented as a charge-coupled device (CCD). The amount (or level) of etching solution in the etching tank is monitored by the level sensor 156. The sensors 150-156 provide analog outputs, so that the flow rate, the temperature, the concentration, and the level of the etching solution are fine-tuned by the respective sensors 150-156.

The RF/matching system 80 includes an RF power system and a matching system. The matching system is used to match input and output impedances in high frequency operation to minimize power loss and improve efficiency. The matching system includes an RF matching network (not illustrated). The RF power system has a plurality of electronic components, such as resistors, capacitors, inductors, transformers, as well as one or more stages of amplifiers. The RF/matching system 80 includes a power sensor 160, a current sensor 162, a temperature sensor 164, an position sensor 166, and an I/O interface 168. The power sensor 160 is used to monitor the input and output powers of the RF matching system 80 to detect potential failures associated with abnormal power loss. The current sensor 162 is used to monitor the current of different stages of amplifiers to determine if the loading of the amplifier is appropriate. The temperature sensor 164 is used to monitor the temperature of the transformers, which has an inverse correlation with its efficiency. The position sensor 166 of the matching system includes a potentiometer (a variable resistor) that is used to cause voltage variations that lead to changes in capacitance and inductance of the RF matching network, which in effect tunes the RF matching network to a desired state. Since capacitance and inductance together define impedance, it can be said that a specific setting of the potentiometer corresponds to a respective impedance of the RF matching network, and thus the impedance sensor 166 monitors the impedance of the RF matching system 80.

The fabrication tools 45-80 may be collectively referred to as a measurement system. The I/O interfaces 118, 122, 127, 135, 146, 158, and 168 of their respective fabrication tools 45-80 are the default I/O interfaces that the respective fabrication tool is equipped with, and the I/O interfaces either do not have the capability to measure the process parameters that the respective sensors of the respective fabrication tools are operable to measure, or that the I/O interfaces do not provide a sufficient number of I/O ports to supply these respective data to external devices. These shortcomings of the I/O interfaces 118, 122, 127, 135, 146, 158, and 168 represent a disadvantage for fabrication tools not equipped with the respective sensors discussed above. However, for the fabrication tools 45-80 discussed above, no such disadvantage exists since these fabrication tools can gather the desired data through their respective sensors.

After the desired fabrication data are gathered by the appropriate sensors, the wireless transceivers 85-92 of the respective fabrication tools 45-80 send the gathered fabrication data across a wireless interface to the diagnostic tool 100. The fabrication data are received by the wireless transceiver 102, which then routes the data to the data miner 105. The data miner 105 then sends the data to the centralized server 110 for detailed processing and analysis. Thereafter, the centralized server 110 makes a determination as to whether the fabrication data fall within an acceptable range. If not, the centralized server 110 may instruct the data miner 105 to send out a signal via the transceiver 102 to tell the appropriate fabrication tool to make adjustments.

Figure 2:
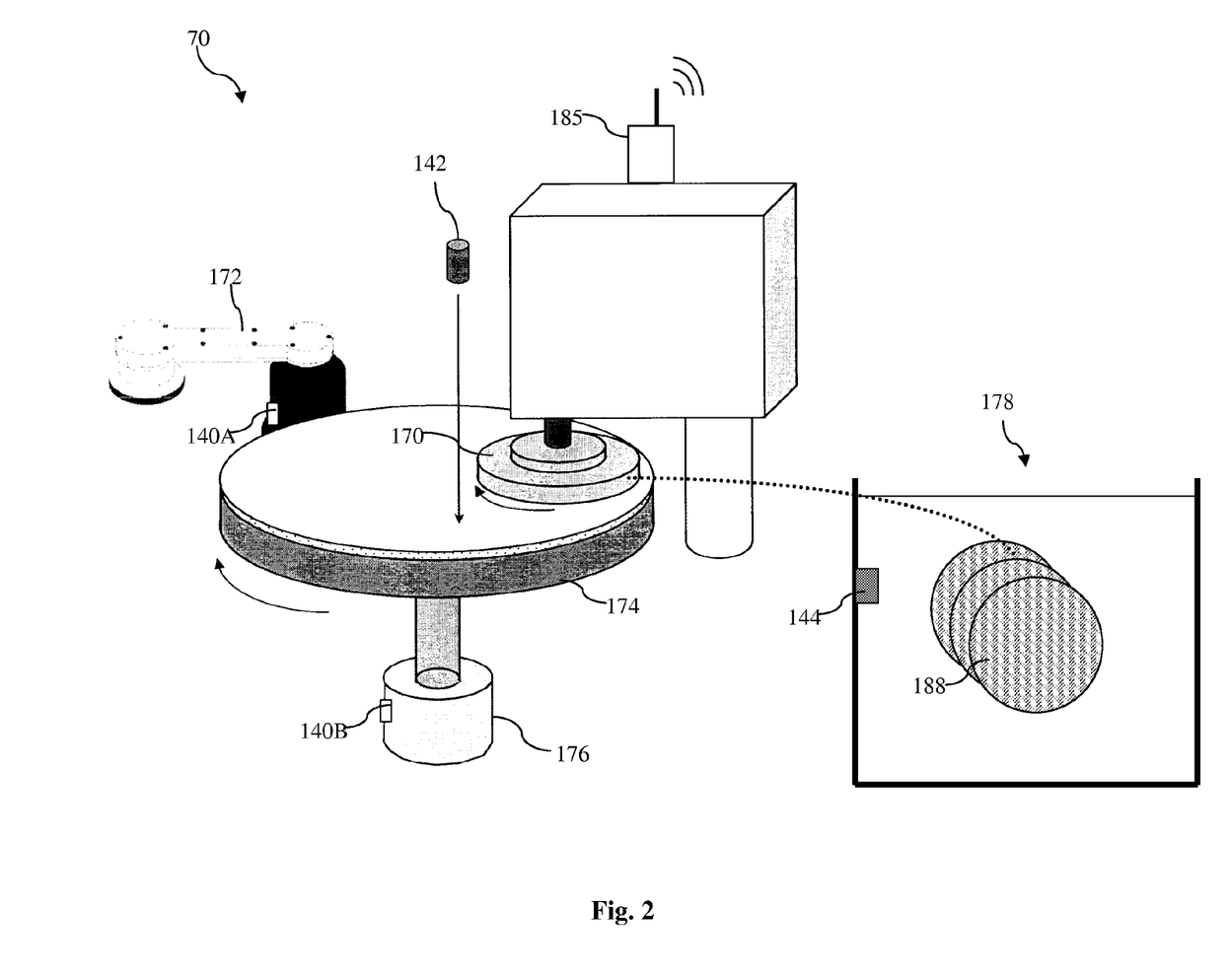
FIG. 2 is a diagrammatic view of an exemplary embodiment of a portion of the semiconductor fabrication system of FIG. 1.

Referring now to FIG. 2, the CMP tool 70 is discussed in more detail so as to provide an example of the operation of the semiconductor fabrication system 40. FIG. 2 illustrates a diagrammatic view of the CMP tool 70 of FIG. 1. The CMP tool 70 includes a polishing head 170, a pad conditioner head 172, a platen 174, a platen gear box 176, a water tank 178 filled with de-ionized water, the sensors 140A-B, 142, and 144 (discussed above with reference to FIG. 1), and a wireless transceiver 185. A semiconductor wafer is secured by the polishing head 170, and the surface of the wafer is polished by the platen 174 as the polishing head 170 moves the wafer across the platen. After polishing, one or more semiconductor wafers 188 are then placed into the water tank 178 to be rinsed with de-ionized water.

The sensor 142 is an infrared radiation detector that is positioned above the platen 174. In an embodiment, the sensor 142 is mounted on the ceiling of a chamber (not illustrated) of the CMP tool 70. The sensor 142 monitors the temperature of the surface of the platen 174 to make sure that the platen is not overheated. Overheating of the surface of the platen 174 indicates high likelihood of failure of the CMP tool 70. The sensors 140A and 140B are vibration sensors implemented as accelerometers and are respectively coupled to the pad conditioner head 172 and the platen gear box 176. The sensors 140A-B monitor the amount of vibration in the CMP tool 70. Excessive vibration also indicates high likelihood of failure of the CMP tool 70. The sensor 144 is a resistance sensor that is coupled to the water tank 178 so as to monitor the resistance of the de-ionized water in the tank. Abnormal resistance variations indicate that the de-ionized water in the water tank 178 is stained by CMP slurry, meaning the de-ionized water has been polluted and needs to be changed.

The heat data, vibration data, and resistance data are respectively gathered by the sensor 142, sensors 140A-B, and the sensor 144, and are thereafter sent to the wireless transceiver 185, which is a Bluetooth transceiver coupled to a suitable portion of the CMP tool 70. The wireless transceiver 185 sends the gathered data wirelessly to the diagnostic tool 100 (FIG. 1) for processing and analysis by the centralized server 110, which is the CIM system of a semiconductor foundry. Depending on the analysis results, the centralized server 110 sends signals back to the CMP tool 70 through the wireless transceivers 102 (FIG. 1) and 185. The CMP tool 70 then adjusts the CMP process accordingly.

In an alternative embodiment for the CMP tool 70 discussed above, each of the sensors 142-144 may have wireless transceivers integrated within, so that each of the sensors 142-144 is capable of wirelessly transferring fabrication data to the diagnostic tool 100 (FIG. 1), as opposed to having to route fabrication data to the standalone wireless transceiver 185 first.

Figure 3:
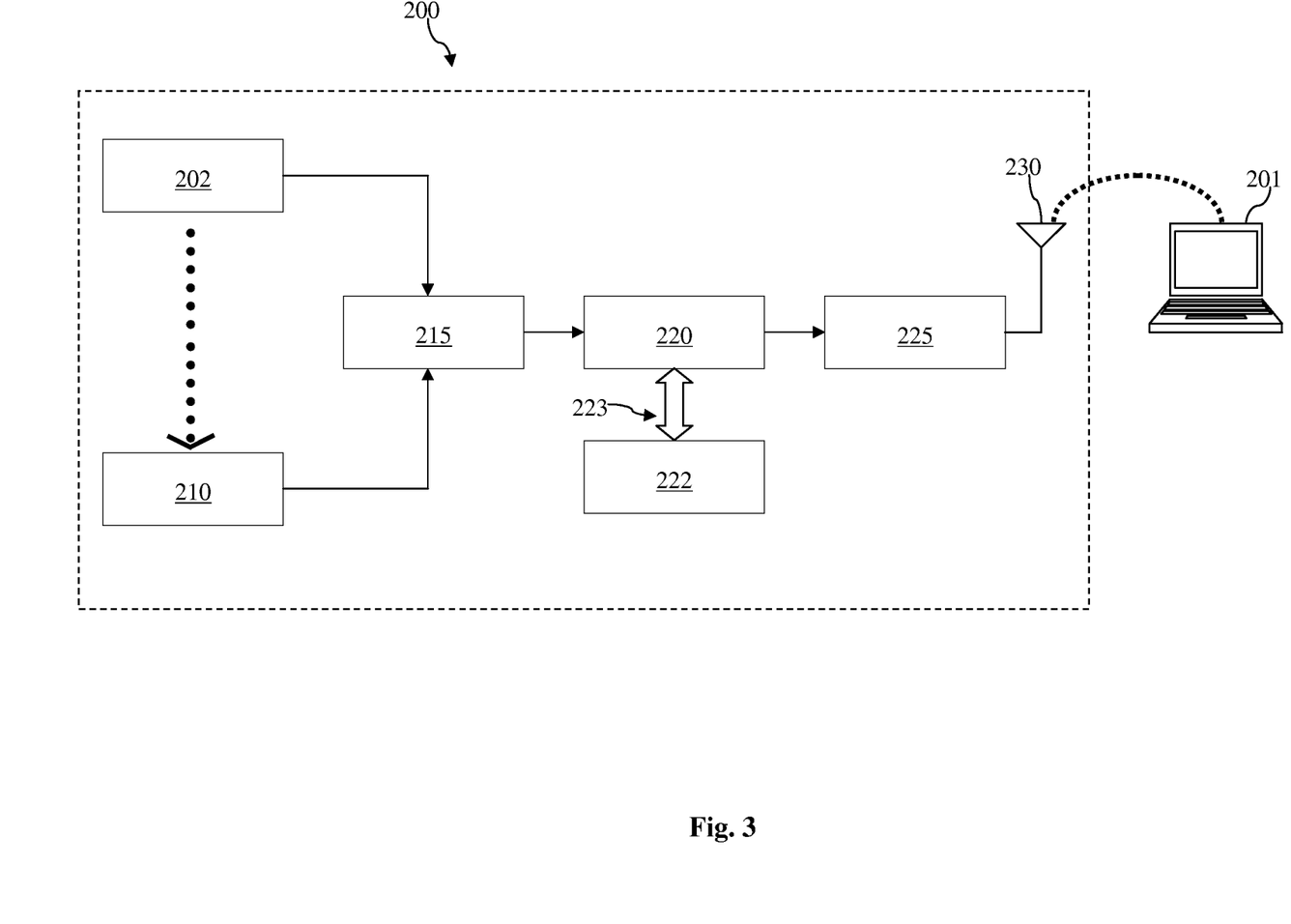
FIG. 3 is a diagrammatic view of a wireless portable multi-function sensor and a diagnostic tool that is wirelessly coupled to the sensor.

FIG. 3 is a diagrammatic view of a wireless portable multi-function sensor (WPMF sensor) 200 and a diagnostic tool 201. The WPMF sensor 200 can be used in place of, or in conjunction with, the wireless transceivers 85-92 and the sensors 112-166 of FIG. 1. In the present embodiment, the WPMF sensor 200 is detachably coupled to a fabrication tool (for example, one of the fabrication tools 45-80 of FIG. 1) to gather fabrication data associated with that tool.

The WPMF sensor 200 includes a plurality of sensors 202 to 210, a signal converter 215, a micro-controller unit (MCU, also referred to as a micro-processor) 220, a storage device 222, a communication interface 223 between the MCU 220 and the storage device 222, and a transceiver 225 that has an optional antenna 230. The sensors 202-210 are similar to the sensors 112-166 discussed above with reference to the FIG. 1 and are used to monitor fabrication data (process parameters) such as voltage, current, resistance, vibration, temperature, etc. The sensors 202-210 output the sensed fabrication data as analog signals. Any number of sensors 202-210 may be implemented in the WPMF sensor 200 depending on design requirements and manufacturing constraints. In alternative embodiments, the sensors 202-210 may be implemented external to the WPMF sensor 200, in which case the WPMF sensor 200 may include ports that are coupled to the external sensors 202-210.

Referring back to FIG. 3, the signal converter 215 receives the output of the WPMF sensors 202-210 as inputs. The signal converter 215 includes a multi-channel analog-to-digital converter in the present embodiment, each channel capable of converting the analog signal output from one of the sensors 202-210 into digital form. In alternative embodiments where the sensors 202-210 output digital signals, the signal converter 215 may perform necessary data processing on the digital signal outputs of the sensors 202-210. The signal converter 215 then outputs the fabrication data to an input of the MCU 220, which performs further processing on the data. In an embodiment, the MCU 220 controls operations of the signal converter 215 and the transceiver 225. In another embodiment, the MCU 220 modulates the data in accordance with a predetermined modulation scheme, such as quadrature phase shift keying (QPSK), quadrature amplitude modulation (QAM), Gaussian frequency shift keying (GFSK), or orthogonal frequency division multiplexing (OFDM). In yet another embodiment, the signal converter 215 is integrated into the MCU 220.

The interface 223 allows the MCU 220 to communicate with the storage device 222. As an example, fabrication data can be transferred between the storage device 222 and the MCU 220 through the interface 223 to enhance the functionalities of the MCU 220. In the present embodiment, the storage device 222 is a secure digital (SD) card, and the interface 223 is an USB port. In alternative embodiments, the storage device 222 may be other forms of memory, including Flash, Memory Stick, Micro-SD, or a hard disk, and the interface 223 may be a serial port, parallel port, FireWire port, or USB port. In yet another alternative embodiment, the storage device 222 may be integrated into the MCU 220.

Referring back to FIG. 3, the fabrication data is sent from an output of the MCU 220 to an input of the transceiver 225 to be broadcast. The transceiver 225 includes a Bluetooth transceiver in the present embodiment. In alternative embodiments, the transceiver 225 may be Wi-Fi or Universal Asynchronous Receiver Transmitter (UART). The antenna 230 is a standalone antenna but may be integrated into the transceiver 225 in alternative embodiments. In further embodiments, the transceiver 225 is integrated into the MCU 220, so that the MCU 220 communicates directly with external devices. In yet another embodiment, the MCU 220 communicates with external devices through the interface 223, or through another suitable interface that is not illustrated. The transmitted fabrication data is received and analyzed by the diagnostic device 201. The diagnostic device 201 includes a laptop computer that has an integrated wireless transceiver (not illustrated) such as a Wi-Fi or a Bluetooth transceiver. Alternatively, the transmitted fabrication data may be received and analyzed by the diagnostic tool 100 of FIG. 1, using the centralized server 110.

The WPMF sensor 200 is portable and can be configured to adapt to a variety of manufacturing and communication platforms. The multiple sensors integrated within the WPMF sensor 200 allow different types of fabrication data to be collected simultaneously. Based on the simultaneously collected fabrication data, a user may then perform a quick analysis using the diagnostic device 201. If the results of the analysis indicate potential problems with the fabrication tool from which the WPMF sensor 200 gathered data, the fabrication tool can be immediately adjusted to prevent manufacturing failures. The adjustment may be made by either a human user or through a computerized feedback control loop.

Figure 4:
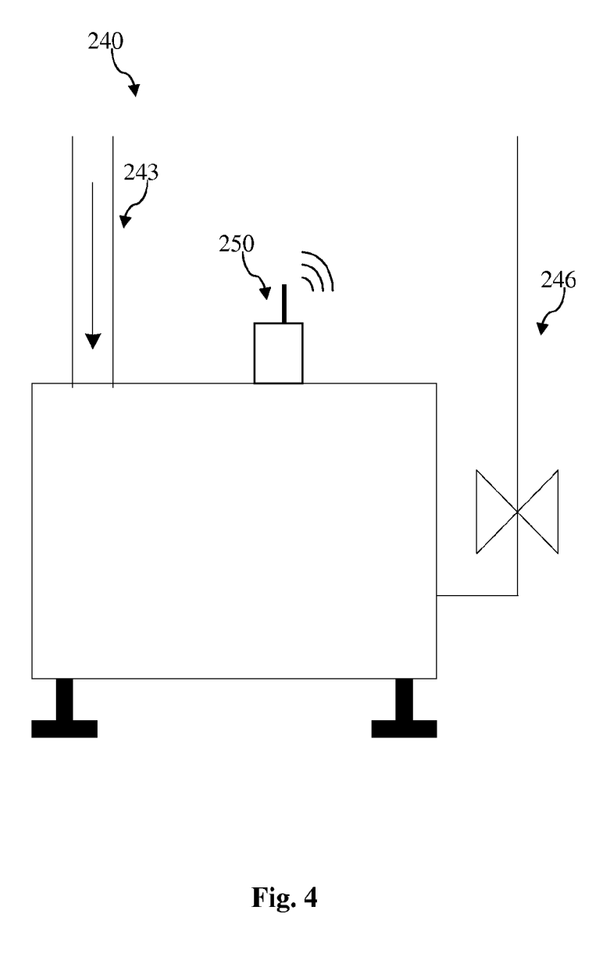
FIG. 4 is a diagrammatic view of an exemplary embodiment and application of the wireless portable multi-function sensor of FIG. 3.

Referring now to FIG. 4, an exemplary embodiment and application of the WPMF sensor 200 is discussed. FIG. 4 illustrates a diagrammatic view of a vacuum pump 240. The vacuum pump 240 includes a process pumping line (inlet) 243, an exhaust pipe (outlet) 246, and a WPMF sensor 250. The vacuum pump 240 is a dry pump in the present embodiment. The vacuum pump 240 may be a cryo-pump in alternative embodiments. Referring back to FIG. 4, the vacuum pump 240 also includes a plurality of internal sensors (not illustrated), including a current sensor that measures motor current (to monitor pump loading), a pressure sensor that measures outlet pressure (to monitor obstruction of the exhaust pipe 246), and a temperature sensor that measures internal pump temperature (to monitor the working temperature of the pump 240).

The WPMF sensor 250 is an exemplary embodiment of the WPMF sensor 200 discussed above with reference to the FIG. 3. The WPMF sensor 250 is placed on an external surface of the vacuum pump 240 and includes a vibration sensor (not illustrated) and a temperature sensor (not illustrated). The vibration sensor is implemented as an accelerometer, and the temperature sensor is implemented as an infrared radiation detector. The vibration sensor monitors the amount of vibration on the vacuum pump 240 during the pump's operation, and the temperature sensor monitors the temperature of the vacuum pump 240 during the pump's operation. When either the vibration or the temperature data is outside an acceptable range but the other parameter is within an acceptable range, action need not necessarily be taken, because the fact that only one process parameter deviates from the normal ranges does not carry much significance. However, when both the vibration and the temperature data are outside the acceptable range, it indicates the vacuum pump 240 is likely to fail soon. Thus, the vacuum pump 240 may be repaired or replaced before actual failure occurs. It is understood that a user may use a laptop to obtain the vibration and temperature data from the vacuum pump wirelessly through the WPMF sensor 250. The user need not perform actual measurements on the vacuum pump 240, since the measurements are automatically made.

Figure 5A:
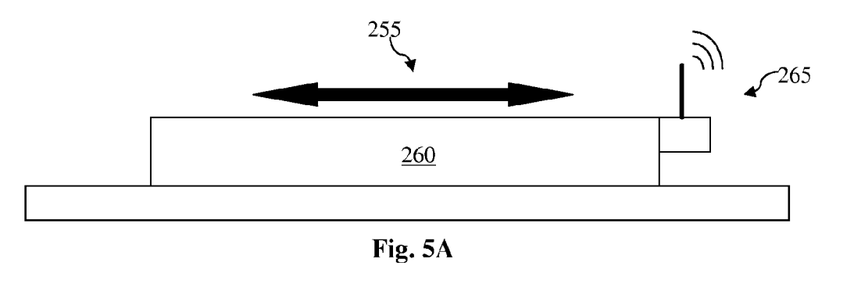
FIG. 5A is a diagrammatic view of another exemplary embodiment and application of the wireless portable multi-function sensor of FIG. 3.

Referring now to FIGS. 5A-5E, another exemplary embodiment and application of the WPMF sensor 200 is discussed. FIG. 5A illustrates a diagrammatic view of an exposure process tool 255. The exposure process tool 255 is used during a photolithography process that forms image patterns on a semiconductor wafer. The exposure process tool 255 includes a moving stage 260 and a WPMF sensor 265. The WPMF sensor 265 is attached to either side of the moving stage 260. In an alternative embodiment, the WPMF 265 is placed over the top surface of the moving stage 260.

Referring back to FIG. 5A, vibrations in the exposure process tool 255 can be caused by defects in various moving components of the exposure process tool 255, including the motor, gear, guider, screw, or bearing (none of which are illustrated). Current fabrication technologies do not provide a measurement of the vibration of the exposure process tool 255. Nonetheless, a relatively small amount of vibration may lead to poor wafer pattern image quality. Further, if the moving stage 260 is not level, the wafers will also have poor pattern image quality. If the wafers having poor pattern image quality are not caught in time, and the wafers undergo etching, they may be unsalvageable and have to be scrapped.

In the present embodiment, the WPMF sensor 265 includes a vibration sensor (not illustrated) and a leveling sensor (not illustrated). The vibration sensor is used to monitor the vibration of the exposure process tool 255, and the leveling sensor is used to monitor the levelness of the moving stage 260, so as to ensure adequate pattern image quality. In the present embodiment, both the vibration sensor and the leveling sensor are implemented as 3-axis micro-electromechanical system (MEMS) accelerometers. The MEMS accelerometer has a relatively high sensitivity to gravity. The sensitivity to gravity is utilized to measure the levelness of the accelerometer (and thus the levelness of the moving stage 260), as discussed below.

Figure 5B:
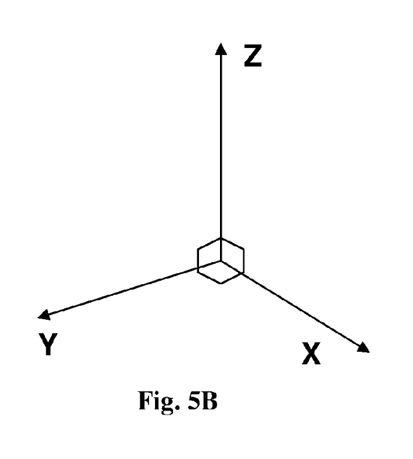
FIG. 5B is a diagrammatic view of a 3-dimensional axes structure illustrating the orientation of the wireless portable multi-function sensor.
Figure 5C:
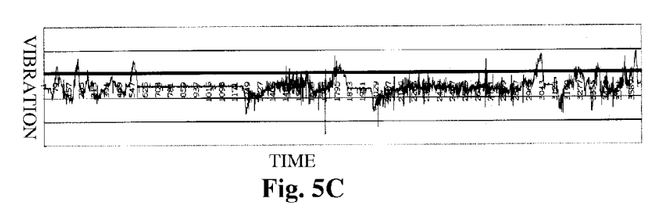
FIGS. 5C-5E are exemplary data plots generated by the wireless portable multi-function sensor of FIG. 5A.
Figure 5D:
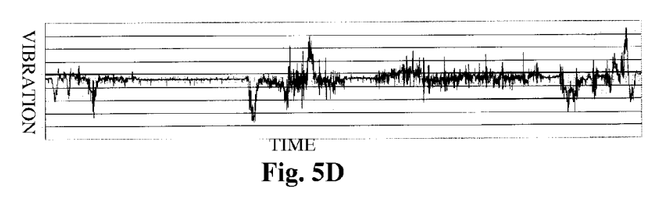
Figure 5E:
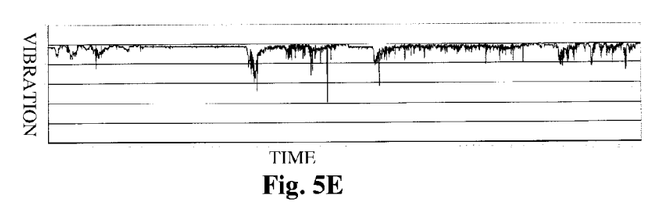

Referring now to FIG. 5B, the orientation of the accelerometer inside the WPMF 265 can be illustrated by the 3-dimensional axes diagram that has an X-axis, a Y-axis, and a Z-axis. The X, Y and Z axes are substantially orthogonal (perpendicular) to one another. The vibrations along each axis are then measured as audio-like signals. Exemplary illustrations of these audio-like signals are shown in FIGS. 5C, 5D, and 5E, where the vertical axis represents vibration signals measured by the accelerometer, and the horizontal axis represents different points in time. FIG. 5C shows vibration signals measured along the X-axis with respect to time, FIG. 5D shows vibration signals measured along the Y-axis with respect to time, and FIG. 5E shows vibration signals measured along the Z-axis with respect to time. Thereafter, data averaging is performed on the measured vibration signals to ensure a more stable reading of the accelerometer. A low pass filter is then used to filter out the high frequency components of the vibration signals, and the remaining portions of the vibration signals are the leveling signals (not illustrated). To view the leveling signals across a frequency spectrum, a fast Fourier transform (FFT) is performed on the vibration signals.

When the accelerometer is substantially level, the leveling signals with respect to the X-axis and the Y-axis should be very close to 0, while the leveling signal with respect to the Z-axis should be 1 times gravity (represented by g). When the accelerometer is tilted (not level), the leveling signals with respect to the X and Y-axes deviate from 0, and the leveling signal with respect to the Z-axis deviates from g. The leveling signals are analyzed (for example, by the diagnostic tool 201 of FIG. 3) so as to indicate how the accelerometer is tilted. As discussed above, the tilt of the accelerometer is indicative of how the WPMF sensor 265 is tilted and therefore how the moving stage 260 is tilted. The moving stage 260 is then adjusted either through a computerized feedback control loop or by a human user, in a manner so that the accelerometer is more level.

It is understood that with respect to its application for the exposure process tool 255, the wireless aspect of the WPMF sensor 265 offers another advantage (it being understood that different advantages are offered by different embodiments): the vibration data would have been unintentionally affected by the cables or wires of a traditional wired sensor, whereas no such cables or wires exist to cause vibration interference in the present embodiment as the WPMF sensor 265 functions wirelessly.

Figure 6:
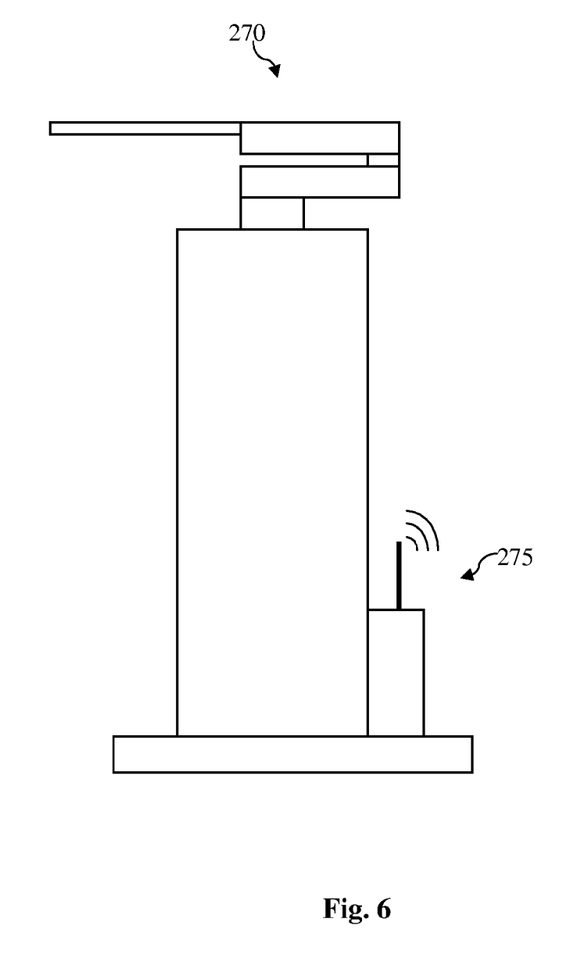
FIG. 6 is a diagrammatic view of a further exemplary embodiment and application of the wireless portable multi-function sensor of FIG. 3.

Referring now to FIG. 6, a further exemplary embodiment and application of the WPMF sensor 200 is discussed. FIG. 6 is a diagrammatic view of a transfer robot 270 that is similar to the transfer robot 45, and on which a WPMF sensor 275 is mounted. The WPMF sensor 275 includes a current sensor, a voltage sensor, and a vibration sensor (none of which are illustrated). The current sensor is used to monitor the current load of a motor (not illustrated) of the transfer robot 270. To control the operation of the motor, digital control signals have to be transformed into analog signals using an encoder (not illustrated). The voltage sensor of the WPMF 275 is used to monitor the voltage of the encoder, so that a phase character can be calculated if the motor is a servo motor, or that a step loss can be calculated if the motor is a stepping motor. The vibration sensor is implemented as an accelerometer and is used to monitor the vibrations of various components of the transfer robot 270 so as to gauge the conditions and performance of these components. Thus, the WPMF 275 gathers fabrication data with respect to motor current, encoder voltage, and transfer robot component vibrations. These gathered fabrication data are wirelessly sent to the diagnostic tool 201 (FIG. 3), either individually or collectively, to determine the quality of the transfer robot 270 and whether it needs to be repaired or overhauled.

The foregoing has outlined features of several embodiments so that those skilled in the art may better understand the detailed description that follows. Those skilled in the art should appreciate that they may readily use the present disclosure as a basis for designing or modifying other processes and structures for carrying out the same purposes and/or achieving the same advantages of the embodiments introduced herein. Those skilled in the art should also realize that such equivalent constructions do not depart from the spirit and scope of the present disclosure, and that they may make various changes, substitutions and alterations herein without departing from the spirit and scope of the present disclosure.

What is claimed is:

1. An apparatus for fabricating a semiconductor device on a semiconductor wafer, the apparatus comprising a portable device that includes:
   first and second sensors that respectively measure first and second fabrication process parameters of one or more fabrication processes performed on the semiconductor wafer, the first fabrication process parameter being different from the second fabrication process parameter; and
   a wireless transceiver that is coupled to the first and second sensors,
   wherein the wireless transceiver is operable to receive the first and second fabrication process parameters and is operable to transmit a first set of wireless signals containing the first and second fabrication process parameters,
   wherein the wireless transceiver is further operable to receive a second set of wireless signals configured to adjust a fabrication process performed on the semiconductor wafer, and
   wherein the portable device is free of being in direct contact with the semiconductor wafer.

2. The apparatus of claim 1, wherein the portable device is detachably coupled to a semiconductor fabrication tool, and wherein the first and second fabrication process parameters are extracted from the fabrication tool.

3. The apparatus of claim 1, wherein the portable device further includes a signal converter and a micro-controller, wherein the signal converter, the micro-controller, the wireless transceiver, and the first and second sensors each have a respective input and a respective output, and wherein:
   the input of the signal converter is coupled to outputs of the first and second sensors;
   the input of the micro-controller is coupled to the output of the signal converter; and
   the input of the wireless transceiver is coupled to the output of the micro-controller.

4. The apparatus of claim 3, further including a storage device that is coupled to the micro-controller through a communication interface, the storage device storing the measured first and second fabrication process parameters.

5. The apparatus of claim 3, wherein the signal converter includes first and second analog-to-digital conversion channels that are respectively coupled to the outputs of the first and second sensors, the first and second analog-to-digital conversion channels respectively converting the measured first and second fabrication process parameters from an analog form into a digital form.

6. The apparatus of claim 1, wherein the portable device is detachably coupled to an external surface of a vacuum pump, and wherein:
the first sensor measures a vibration of the vacuum pump as the first fabrication process parameter; and
the second sensor measures a temperature of the vacuum pump as the second fabrication process parameter.

7. The apparatus of claim 1, wherein the portable device is detachably coupled to a moving stage of an exposure process tool, and wherein:
the first sensor measures a vibration of the exposure process tool as the first fabrication process parameter; and
the second sensor measures a levelness of the moving stage as the second fabrication process parameter.

8. The apparatus of claim 1, wherein the portable device is detachably coupled to a transfer robot that has a motor and an encoder that controls the motor, and wherein:
the first sensor measures a current load of the motor as the first fabrication process parameter; and
the second sensor measures a voltage of the encoder as the second fabrication process parameter.

9. An apparatus for fabricating a semiconductor device, the apparatus comprising a portable device that includes:
first and second sensors that measure first and second processing data in an analog form;
a signal converter that converts the first and second processing data from the analog form into a digital form;
a micro-controller that modulates the measured first and second processing data using a predetermined modulation scheme; and
a wireless transceiver that transmits a first set of wireless signals containing the modulated first and second processing data,
wherein the first and second processing data measured by the first and second sensors correspond to one or more processes performed on a semiconductor substrate on which the semiconductor device is fabricated,
wherein the wireless transceiver is operable to receive a second set of wireless signals configured to adjust a fabrication process, and
wherein the portable device is free of being in physical contact with the semiconductor substrate.

10. The apparatus of claim 9, wherein the micro-controller includes a data storage device that stores one of the measured first and second processing data and the modulated first and second processing data, and wherein the micro-controller controls the signal converter and the wireless transceiver.

11. The apparatus of claim 9, wherein the first and second processing data are different types of data.

12. The apparatus of claim 9, wherein the signal converter and the wireless transceiver are integrated into the micro-controller.

13. A method of fabricating a semiconductor device on a wafer, comprising:
measuring a first fabrication process parameter using a first sensor;
measuring a second fabrication process parameter using a second sensor, the second fabrication process parameter being different from the first fabrication process parameter, wherein the measuring of the first fabrication process parameter and the measuring of the second fabrication process parameter are performed such that the first and second sensor are free of being in physical contact with the wafer;
transmitting a first set of wireless signals containing the measured first and second fabrication process parameters using a wireless transceiver;
receiving a second set of signals through the wireless transceiver, wherein the second set of signals is configured to adjust a fabrication process performed on the wafer; and
configuring the wireless transceiver and the first and second sensors so that the wireless transceiver and the first and second sensors are integrated into a single portable device.

14. The method of claim 13, wherein:
the measuring the first fabrication process parameter includes extracting the first fabrication process parameter from a semiconductor fabrication tool; and
the measuring the second fabrication process parameter includes extracting the second fabrication process parameter from the semiconductor fabrication tool.

15. The method of claim 13, further including:
converting the measured first and second fabrication process parameters from an analog form into a digital form using a signal converter;
modulating the measured first and second fabrication process parameters using a micro-controller; and
storing the measured first and second fabrication process parameters using a storage device.

16. The method of claim 15, further including controlling the wireless transceiver and the first and second sensors using the micro-controller.

17. The method of claim 13, further including detachably coupling the portable device to an external surface of a vacuum pump, and wherein:
the measuring the first fabrication process parameter includes measuring a vibration of the vacuum pump using an accelerometer as the first sensor; and
the measuring the second fabrication process parameter includes measuring a temperature of the vacuum pump using an infrared radiation detector as the second sensor.

18. The method of claim 13, further including detachably coupling the portable device to a moving stage of an exposure tool, and wherein:
the measuring the first fabrication process parameter includes measuring a vibration of the exposure tool using a first accelerometer as the first sensor; and
the measuring the second fabrication process parameter includes measuring a levelness of the exposure tool using a second accelerometer as the second sensor.

19. The method of claim 18, wherein the measuring the levelness includes:
measuring first, second, and third vibration signals along first, second, and third axes of the further accelerometer, respectively, the first, second, and third axes being orthogonal with respect to one another;
averaging the first, second, and third vibration signals;
filtering the first, second, and third vibration signals using a low pass filter so that high frequency components of the first, second, and third vibration signals are eliminated; and
converting the first, second, and third vibration signals from a time domain to a frequency domain to obtain first, second, and third leveling signals with respect to the first, second, and third axes.

20. The method of claim 13, further including detachably coupling the portable device to a transfer robot that has a motor and an encoder that controls the motor, and wherein:
    the measuring the first fabrication process parameter includes measuring a current load of the motor using a current sensor as the first sensor; and
    the measuring the second fabrication process parameter includes:
        measuring a voltage of the encoder using a voltage sensor as the second sensor; and
        calculating one of a phase character and a step loss in response to the measured voltage.

\* \* \* \* \*